United States Patent
Timmer

(10) Patent No.: US 7,919,765 B2
(45) Date of Patent: Apr. 5, 2011

(54) NON-CONTINUOUS PARTICLE BEAM IRRADIATION METHOD AND APPARATUS

(75) Inventor: Jan Timmer, Cologne (DE)

(73) Assignee: Varian Medical Systems Particle Therapy GmbH, Bergisch-Gladbach (DE)

( * ) Notice: Subject to any disclaimer, the term of this patent is extended or adjusted under 35 U.S.C. 154(b) by 430 days.

(21) Appl. No.: 12/077,792

(22) Filed: Mar. 20, 2008

(65) Prior Publication Data
US 2009/0236545 A1    Sep. 24, 2009

(51) Int. Cl.
*A61N 5/10*    (2006.01)
(52) U.S. Cl. .................. 250/505.1; 250/492.3
(58) Field of Classification Search .............. 250/492.3, 250/505.1
See application file for complete search history.

(56) References Cited

U.S. PATENT DOCUMENTS
6,717,162 B1 * 4/2004 Jongen ........................ 250/505.1
7,432,516 B2 * 10/2008 Peggs et al. ................. 250/492.3

OTHER PUBLICATIONS

Padroni et al., "The 200-MeV proton therapy project at the Paul Scherrer Institute: Conceptual design and practical realization," Am. Assoc. Phys. Med., 22(1):37-53, Switzerland, Jan. 1995.
Chu et al., "Instrumentation for treatment of cancer using proton and light-ion beams," Rev. Sci. Instrum., 64(8):2055-2122, New York, Aug. 1993.

* cited by examiner

*Primary Examiner* — Kiet T Nguyen
(74) *Attorney, Agent, or Firm* — Alleman Hall McCoy Russell & Tuttle LLP

(57) ABSTRACT

Method and apparatus are disclosed for treating a non-continuous particle beam produced by an accelerator in order to irradiate a target volume, wherein an irradiation spot located in the target volume is formed from this beam, and wherein the location of the irradiation spot is controlled by location controlling elements. The setting of the location controlling elements may take place in between subsequent particle bunches of the beam, for example.

27 Claims, 3 Drawing Sheets

NON-CONTINUOUS PARTICLE BEAM IRRADIATION METHOD AND APPARATUS

BACKGROUND

The present disclosure relates to a method for irradiating an irradiation target with a non-continuous particle beam, in particular a proton beam. Furthermore, the present disclosure relates to an apparatus for carrying out said method.

Charged particle beams consisting of protons or heavier ions are successfully used in cancer therapy to destroy tumors by irradiation. One of the advantages of such charged particle beams is the Bragg peak at the end of the beam path where a large fraction of the irradiation dose is deposited. The depth of the Bragg peak can be varied by varying the particle beam energy. This allows for control of the irradiation depth and, in combination with lateral beam spreading or deflection, a good three dimensional dose conformation, i.e. an effective delivery of the dose to the target volume (tumor) while avoiding damages in neighboring regions (healthy tissue).

A charged particle therapy system is for example described in U.S. Pat. No. 5,260,581. Charged particle therapy systems usually comprise an accelerator for producing a charged particle beam, a beam transport system for transporting the beam to the patient, and various means for treating the beam in order to achieve a good conformation of the dose to the target volume. The term "treating the beam" shall encompass all possible forms of manipulating the beam, including, without limitation, focusing, spreading, deflecting and interrupting the beam and changing the energy of the beam particles.

Various types of particle accelerators are used in charged particle therapy, inter alia synchrotrons and cyclotrons. In synchrotrons, particles are accelerated in an orbit resulting from a magnetic field that is actively changed with time to keep the orbital radius constant. The beam extracted from a synchrotron is not continuous but pulsed in discrete bunches. The discrete beam bunches are extracted from a synchrotron with the same frequency as with which the magnetic field is cycled. By a method called "slow extraction", the beam bunch accelerated in a synchrotron can be gradually extracted over time. Elongated pulses can be extracted such that a semi-continuous beam can be generated. During the time of slow extraction, which can be several seconds long, the extracted beam is continuous, but after extraction of the accelerated bunch, the magnetic field must be cycled again and the beam is interrupted. A synchrotron allows the energy of the extracted particles to vary over a broad range.

A cyclotron is a circular accelerator which has a magnetic field constant over time but with the magnetic field strength changing with the radius. A particle accelerated in a cyclotron moves on a spiral path with increasing radius in the plane normal to the magnetic field. Particles are accelerated in a cyclotron by applying an alternating radio frequency (RF) voltage to one or more electrodes, called "dees". The RF voltage generates an electric filed across the gap between the adjacent dees. The orbital period of the charged particles in the magnetic field must be synchronized to the RF voltage so that the particles are effectively accelerated as they repeatedly cross the dee gaps. The synchronization must be adjusted in such a way that also relativistic mass effects are compensated for.

Two different types of cyclotrons have been developed that solve the synchronization between orbital period and RF voltage in different ways. The "isochronous cyclotron" uses a constant frequency of the voltage and has a magnetic field that increases with the radius. The shape of the magnetic field compensates for the relativistic mass increase of the charged particles with acceleration. Thereby, the isochronous cyclotron is capable of producing a continuous beam without interruptions.

In a synchrocyclotron the magnetic field is constant or decreasing with increasing radius of the accelerator and the RF frequency of the accelerating voltage is adjusted to achieve synchronization with the orbital period of the charged particles. The RF frequency of the acceleration is changed (modulated) in a cycle, starting at the highest or "injection" frequency and decreasing over time to the lowest frequency or "extraction" frequency. After reaching the extraction frequency, the modulation cycle is started again with the injection frequency. As a consequence, a synchrocyclotron can only accelerate one discrete bunch of charged particles per RF frequency modulation cycle to the final accelerator energy. The time structure of a particle beam extracted from a synchrocyclotron is pulsed as only particles are extracted when the RF frequency of the accelerating voltage is equal to the extraction frequency. The length of the particle bunch from a synchrocyclotron is typically in the order of $10^5$ times shorter than a bunch extracted from a synchrotron using slow extraction.

In all types of accelerators described above, the RF accelerating voltage imposes a "micro-structure" on the beam in the longitudinal direction. The inverse of the frequency or period of the accelerating voltage is orders of magnitude smaller than the time constants relevant for operating charged particle therapy apparatus, such as the setting time of scanning magnets and energy degraders, the measurement time needed by beam diagnostic means, or the bunch length produced by synchrotrons and synchrocyclotrons or other accelerators. Therefore, the RF micro-structure of the beam or beam-bunches is neglected in the remainder of this document.

In charged particle therapy various methods are known to achieve a good dose conformation to the target volume. They are usually grouped into "passive" methods and "active" methods which are inter alia described in W. Chu et al. (Rev. Sci. Instrum. 64, pp. 2055 (1993)). Passive systems generally use scattering systems in order to broaden the beam and to cover the treatment areas required in charged particle therapy. However, expensive patient specific equipment is required and neutrons generated in the scattering systems lead to unwanted increased neutron doses for the patient.

According to active methods, for example described in W. Chu et al. (Rev. Sci. Instrum. 64, pp. 2055 (1993)), the beam is deflected and scanned over the target, for example by use of deflection magnets. Some active methods require patient specific path compensators, bolus or collimators which increase effort and cost of the treatment. This is avoided by an active method known as "pencil beam scanning" or "spot scanning" which is described in E. Pedroni et al. (Med. Phys. 22 (1), 1995). Pencil beam scanning uses continuous or semi-continuous beams. The irradiation spot is moved in the distal direction, i.e. in the direction of the beam, by changing the energy of the beam, most commonly by using an energy degrader. The movement of the beam in the X- and Y-direction in the plane normal to the direction of the beam is performed with two scanning magnets. By using a focused "pencil beam" individual small volumes, also referred to as "voxels", can be treated. The whole tumor is subdivided into voxels and then irradiated voxel by voxel. During treatment, the beam is moved to a specific voxel, and this voxel is irradiated until a dose monitor detects that the required dose level for this voxel has been reached. The (semi-)continuous beam is turned off, and the machine parameters are adjusted for the next voxel. In order to avoid imprecise dose application, the beam switch has to be fast and exact and the intensity has to be kept at a lower level which leads to lengthy treatment times. Several techniques are used in pencil beam scanning to tune the motion and the intensity of the beam in order to regulate the dose applied to each voxel. In some methods, the movement of the beam in three dimensions is performed without interrupting the beam. In other methods, the beam is interrupted after the irradiation of a single voxel. In this case, the irradiation is re-started after the two scanning magnets and the energy degrader have reached the settings needed for the next voxel. However, in all these methods a continuous or semi-continuous beam, for example from an isochronous cyclotron or a synchrotron with slow extraction, is used to irradiate a single voxel.

The use of a non-continuous (pulsed) beam with known pencil beam techniques leads either to very long treatment times or to imprecise dose application. The bunch length of a non-continuous beam is usually too short to be interrupted or subdivided. Therefore, if the required dose precision per voxel is +/−2%, a single bunch of particles can only have 2% of the total dose per voxel, so that 50 bunches are needed per voxel. This leads to undesirable long treatment times. Furthermore, the techniques used to avoid imprecisions due to organ motion lengthen treatment times. One of such techniques is gating, i.e. setting a treatment window such that irradiation is only applied during certain phases of organ motion, e.g. during certain phases of the breathing cycle of the patient. Another technique to mitigate the effects of organ motion is to average out the movements by irradiating all voxels multiple times. All of these techniques lead to even longer treatment times.

Pencil beam scanning has several advantages with respect to other active or passive methods. The dose conformation can be significantly improved, the neutron dose for the patient can be decreased and the time consuming and costly process of production and mounting of patient specific compensators and collimators can be omitted. However, according to current techniques, pencil beam scanning can only be performed with continuous or semi-continuous beams. The particle accelerators typically needed to produce such (semi-)continuous beams, for example isochronous cyclotrons and synchrotrons with slow extraction, are usually mechanically larger than accelerators producing a non-continuous or pulsed particle beam such as synchrocyclotrons or linear accelerators (linacs).

SUMMARY

One or more embodiments of the present disclosure aim to provide a method and an apparatus for treating a target volume with a particle beam which avoid the drawbacks of the methods and devices described previously, while at the same time making it possible to deliver a dose to the target volume with high flexibility. One or more embodiments of the present disclosure aim to make it possible to deliver well defined irradiation doses to the target volume with a focused non-continuous beam, generated for example by a synchrocyclotron. Furthermore, one or more embodiments of the present disclosure aim to make it possible to treat patients with a non-continuous particle beam with a low neutron dose received by the patient. Moreover, one or more embodiments of the present disclosure aim to achieve short treatment times while assuring a good dose conformation. Furthermore, one or more embodiments of the present disclosure aim to provide a method and an apparatus allowing to measure and/or control the intensity or bunch charge extracted from an accelerator producing a non-continuous beam.

In a first aspect, the present disclosure suggests a method for treating a non-continuous particle beam which is produced by an accelerator in order to irradiate a target volume, for example of a cancerous tumor. An irradiation spot located in the target volume is formed from the non-continuous particle beam. The location of the irradiation spot is controlled by location controlling elements. According to an embodiment of the present disclosure, the method is characterized in that the setting of the location controlling elements takes place in between subsequent particle bunches of the non-continuous particle beam. In an example embodiment, the location controlling elements control the location of the irradiation spot in three dimensions (X-, Y-, Z-direction) and the setting in the three dimensions takes place in between subsequent bunches. For example, the location controlling elements may comprise an energy degrader for controlling the location of the irradiation spot in the direction of the beam (Z-direction) and/or scanning magnets for controlling the location of the irradiation spot in the plane perpendicular to the beam (X- and Y-directions). In an example embodiment, the setting of the irradiation spot in the two directions perpendicular to the beam (X- and Y-direction) takes place in discrete steps between the bunches. A piece of material of variable thickness may be used as an energy degrader by inserting into the beam in order to decelerate the beam particles. In an alternate embodiment an active energy manipulator may be used to control the location of the irradiation spot in the Z-direction. Such an active energy manipulator may be a linear accelerator/decelerator which increases or decreases the energy of the beam particles. Such linear accelerators are partly also known as linac boosters (LIBOs). In a further alternate embodiment, the accelerator producing the charged particle beam itself constitutes a location controlling element for controlling the location of the irradiation spot in the Z-direction. Such embodiments use accelerators which produce beams with variable beam energy, for example synchrotrons or linear accelerators consisting of multiple cavities or multiple acceleration stages allowing the energy to change by switching on and off these stages.

In an example embodiment, the accelerator accelerates the particles in repeating acceleration cycles leading to a non-continuous particle beam with particle bunches of a finite length. The setting of the location controlling elements is synchronized with the repetition of the acceleration cycle. In particular, the accelerator may comprise, like a synchrocyclotron, an RF-system for alternating the accelerating voltage with an RF-frequency, whereby the RF-frequency is changed (modulated) in a cycle. In an example embodiment, the setting of the location controlling elements is synchronized with the RF-frequency modulation cycle such that the setting of the location controlling elements takes place between the bunches without interrupting the RF-frequency modulation cycles. In an alternate example embodiment, the RF-frequency modulation cycle is actively interrupted by a control system to allow sufficient time-between the bunches to finish the setting of the location controlling elements.

In another example embodiment, signals from current diagnostic means and/or signals from the RF system of the accelerator are used to detect the period between the bunches. Current diagnostic means measure the current of the charged particle beam. For online current measurement, i.e. measurement during treatment of the patient, gas filled ionisation chambers can be used. Such ionisation chambers are typically mounted in the irradiation head or nozzle, not far from the patient. The electrical signal from the ionisation chamber is converted into a current signal by use of an energy dependent conversion factor. Alternatively, a secondary emission monitor can be used as a current diagnostic means for online current measurement. A secondary emission monitor is usually only used to measure higher currents and is therefore often mounted upstream of an energy degrader.

In another example embodiment, the time between subsequent bunches is actively changed, in particular lengthened, by a control system controlling the repetition rate of the acceleration cycles and/or the RF-system of the accelerator and/or the ion source and/or the input deflector deflecting the ions from the ion source into the accelerator. This allows for increasing the time between the bunches for setting the location controlling elements.

According to another example embodiment of the present disclosure, the number of charged particles in each bunch is actively controlled for optimum dose conformation and/or minimum irradiation time per voxel. For example, the parameters of the accelerator and/or the beam transport system and/or other elements affecting the beam are set such that the number of charged particles in a single bunch matches the total dose needed for a specific voxel in the target. Some of the elements affecting the beam may be located at the end of the beam transport system in the irradiation head from which the beam is directed to the patient.

In an alternate embodiment, the parameters of the accelerator and/or the beam transport system and/or the other elements affecting the beam are set such that the number of particles in a single bunch is part of the total dose needed for a specific voxel in the target. In this case, multiple bunches are needed to match the total dose needed for the specific voxel. Preferably, in order to optimize the dose conformation and reduce the irradiation time per voxel, within a series of bunches irradiated to a specific voxel, earlier bunches have a higher number of particles than later bunches. More preferably, the number of charged particles per bunch is decreased within a series of bunches irradiated to a specific voxel. The first bunch with which a specific voxel is irradiated, has a high number of particles and the number of particles is decreased in the subsequent bunches irradiated onto this voxel such that the last bunches have only a low number of particles. This allows a precise application of the dose to the voxel at a reduced treatment time.

In another example embodiment, the number of particles of a bunch is measured by dose diagnostic means, and the control system calculates the desired number of particles in the next bunch and controls the elements affecting the beam in such way that the next bunch contains the desired number of particles. For example, an ionisation chamber can be used as a dose diagnostic means for online dose measurement.

In a further aspect, the present disclosure suggests an apparatus for carrying out the above method. Such apparatus comprises a particle accelerator, for example a synchrocyclotron for obtaining a non-continuous particle beam consisting of discrete consecutive particle bunches, a beam transport system for transporting the beam to the target volume and location controlling elements for controlling the location of an irradiation spot formed in the irradiation target. The apparatus is characterized in that it comprises a control system controlling the location controlling elements in such way that the setting of the location controlling elements takes place in between subsequent particle bunches.

In an example embodiment, the apparatus comprises charge variation means for varying the number of charged particles per bunch. For example, the number of charged particles per bunch is manipulated with a deflector located inside the vacuum chamber of the accelerator. The deflector may consist of two electrically conducting plates mounted above and below the accelerating plane of the accelerator. For example, the two plates of the deflector are located in a region of the accelerator where the particles being accelerated still have a limited energy. By applying a voltage to the two plates of the deflector using one or more voltage sources, the low energy beam can be deflected in the direction normal to the accelerating plane. Depending on the voltage applied to the plates of the deflector, a smaller or larger part of the particle bunches is stopped on collimator plates mounted above and below the accelerating plane. The voltage applied to the conducting plates of the deflector can be used to control the number of charged particles in an extracted particle bunch. If the deflector is located in a region where the energy of the charged particles is low, the voltage needed between the conducting plates of the deflector to deflect part of the bunch onto the collimator plates is limited and the radiation generated by the particles stopped on the collimator plates is also limited.

In an alternate embodiment, the ion source of the accelerator can be used to adjust the number of charged particles per bunch. Three different methods may be used to adjust the number of charged particles being injected by the ion source for acceleration. The parameters of the ion source itself can be adjusted, such as the arc current, the filament current, the gas flow and RF power in case of an external source. Secondly, the voltage or the potential of the extraction electrodes can be set. Thirdly, in case of an external ion source, an electromagnetic or mechanical element in the low energy beam line between the ion source and the accelerator can be used to adjust a number of charged particles per bunch. Such an element can have the form a mechanical variable collimator with drive or the form of an electrical deflector. Furthermore, a device commonly called a "buncher" can be used to adjust the number of charge particles per bunch. In addition, for final adjustments of the number of charged particles per bunch, the RF system of the accelerator may be used to adjust the number of charge particles per bunch.

BRIEF DESCRIPTION OF THE FIGURES

An embodiment of the present disclosure will be further described with the attached figures in which.

DETAILED DESCRIPTION OF THE FIGURES

Figure 1:
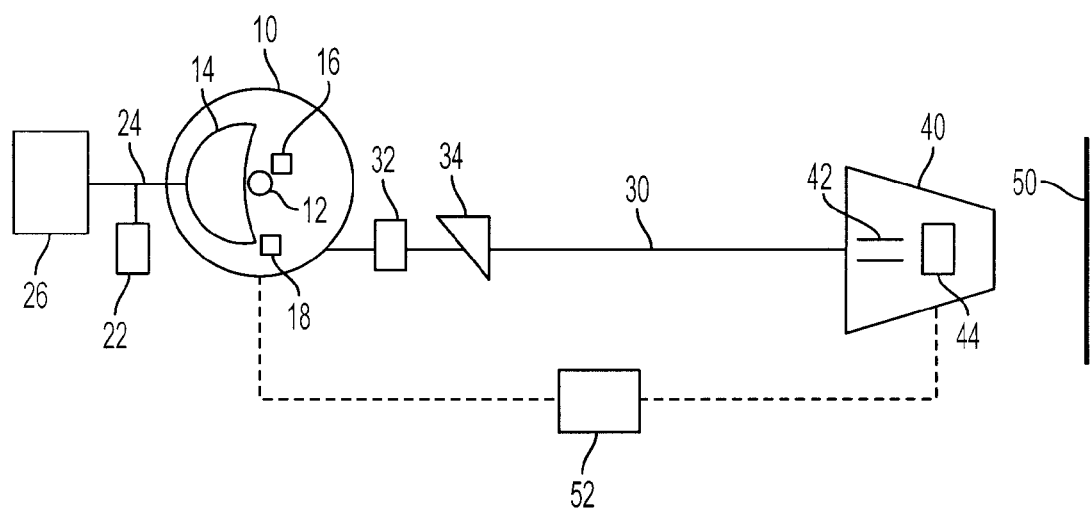
FIG. 1 shows a schematic view of an apparatus according to an embodiment of the present disclosure.

An example embodiment of the present disclosure will now be described with the aid of the figures. FIG. 1 shows an example of an apparatus according to an embodiment of the present disclosure which is suitable for carrying out a method according to one of the embodiments of the present disclosure. The apparatus comprises a synchrocyclotron 10 as an accelerator for producing a non-continuous particle beam of protons or heavier ions. The charged particles to be accelerated are delivered to the accelerator by an ion source 12. One of the dees 14 of the accelerator is also shown in FIG. 1. Located inside the vacuum chamber of the synchrocyclotron 10 there is a vertical deflector 16 for controlling the number of charged particles to be accelerated and an internal current measurement means 18 for measuring the number of charged particles in the beam. The RF-system of the accelerator 10 comprises an RF amplifier 20, a frequency manipulator 22 such as a rotating capacitor 22 or tuning panels and an RF tube 24 between the RF amplifier 20 and the accelerator 10. A non-continuous particle beam is extracted from the synchrocyclotron 10. The beam consists of a series of discrete particle bunches. From the synchrocyclotron 10 the beam is transported by a beam transport system 30 to the irradiation head 40, which is also called "nozzle". From the nozzle 40 the beam is directed to the irradiation target, i.e. to the patient 50. On its way from the synchrocyclotron 10 to the nozzle 40, the beam current, i.e. the number of charged particles per bunch, is measured by external current measurement means 32, for example a secondary emission monitor. Furthermore, the beam is run through an energy degrader 34 for adjusting the energy of the beam particles to a desired value in order to control the irradiation depth of the beam in the irradiation target 50. The nozzle 40 comprises deflection or scanning magnets for varying the position of the beam in the plane perpendicular to the beam direction. One pair of scanning magnets 42 is shown in FIG. 1 which may be for example used for deflection of the beam in X-direction. Another pair of scanning magnets for deflection in Y-direction is not shown in FIG. 1. Furthermore, the nozzle 40 comprises dose diagnostic means 44, for example an ionisation chamber, for measuring the dose delivered to the irradiation target. An irradiation control system 52 controls all functions and elements of the apparatus. Signals from the RF-system and the current and dose diagnostic means are fed into the control system. The control system controls all relevant elements of the accelerator, beam transport system and irradiation head in such way that the setting of the location controlling elements controlling the location of the irradiation spot, i.e. the energy degrader 34 and the scanning magnets 42, takes place in between subsequent particle bunches. Moreover, the irradiation control system 52 controls the number of charged particles in each bunch actively in order to achieve optimum dose conformation and/or minimum irradiation time per irradiated volume element (voxel).

Figure 2:
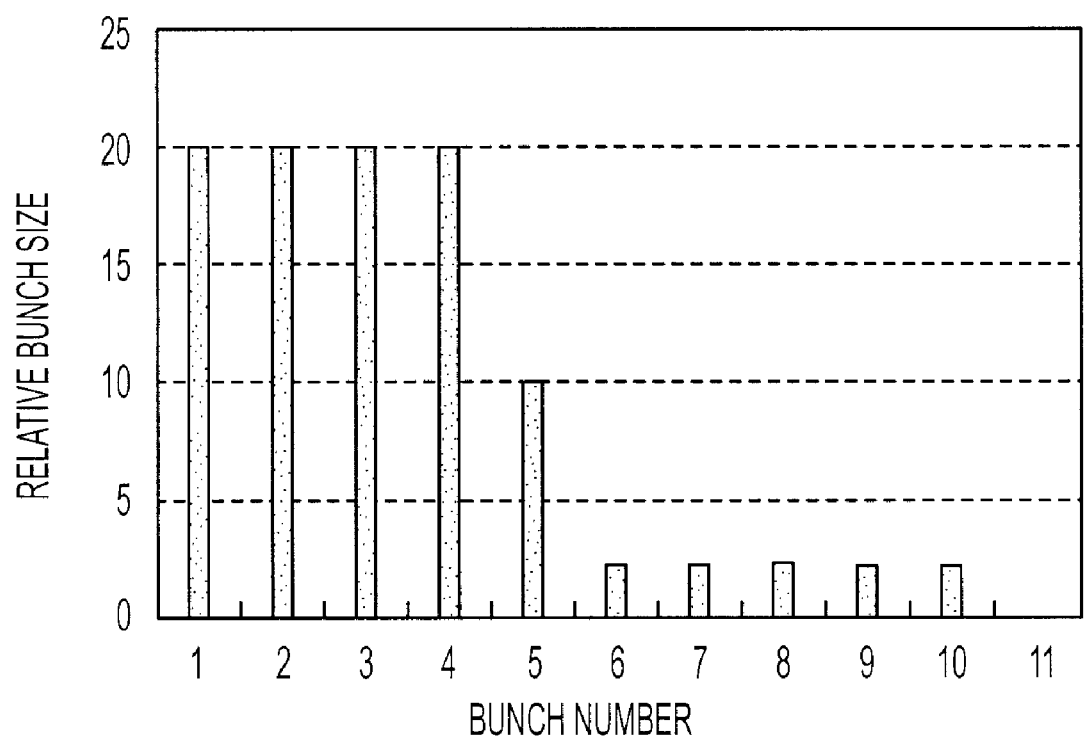
FIG. 2 shows an example of a sequence of particle bunches with a varying number of charged particles per bunch.

FIG. 2 shows a sequence of particle bunches irradiated to a specific voxel. As shown in FIG. 2, the number of charged particles per bunch is varied is such way that the first bunches irradiated to the specific voxel have a high number and the later bunches have a lower number of charged particles. The first four bunches carry 20% of the total dose for this voxel, the fifth bunch 10% and the last 5 bunches 2%. So the total dose for this voxel is applied by a series of 20%-20%-20%-20%-10%-2%-2%-2%-2%-2% bunches. Compared to a series of 50 bunches with 2%, such pattern reduces the treatment time significantly without affecting the precision of the dose application. Certainly, bunches of other size than shown in FIG. 2 can also be used. In general, when irradiating a voxel with multiple bunches, it is preferable to have at least one bunch whose percentage of the desired dose is not greater than the desired dose precision, more preferably to have two such bunches. More generally, the size of the bunches may be selected based on the principle that bunches with larger increments of the desired dose increase the speed of the treatment, while bunches with smaller dose increments allow a better control of the desired dose for a specific voxel.

Figure 3A:
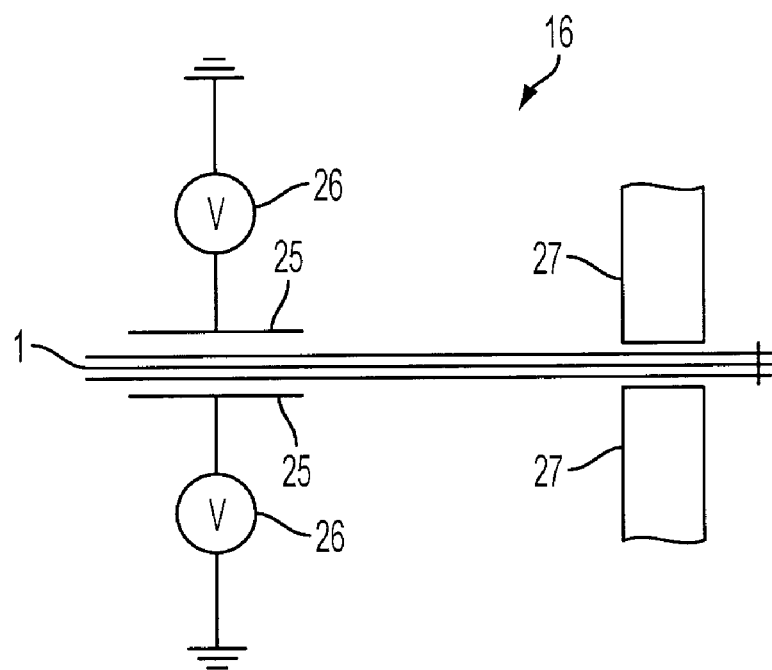
FIG. 3a and 3b show a schematic view of a deflector 16 for controlling the number of charged particles per bunch.
Figure 3B:
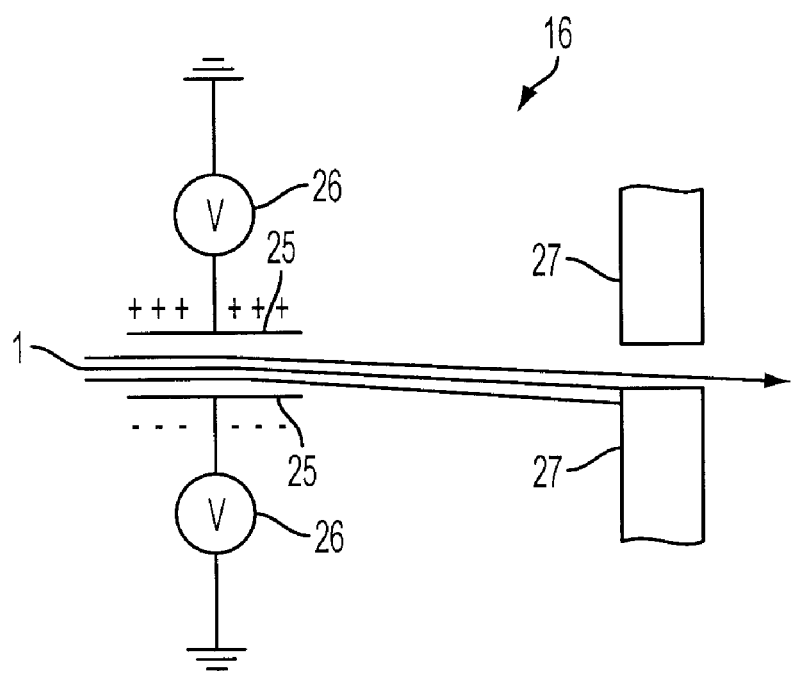

FIGS. 3a and 3b show a detailed view of the vertical deflector 16 in the synchrocyclotron 10. The vertical deflector comprises electrically conducting deflection plates 25 for deflecting the beam 1 by application of a voltage 26. If no voltage 26 is applied to the deflection plates 25, the beam passes straight forward through the collimator plates 27 as shown in FIG. 3a. However, if a voltage 26 is applied to the deflection plates 25 as shown in FIG. 3b, the beam is deflected and partly stopped by the collimator plates 27. This way, the vertical deflector 16 may control the number of charged particles per bunch. This allows generation of sequences of bunches with different numbers of charged particles as shown in FIG. 2.

All in all, the embodiments of the present disclosure may provide one or more of the following advantages. Some embodiments allow the use of all types of accelerators producing non-continuous particle beams, in particular the use of a comparatively small and cost effective synchrocyclotron, but also the use of new accelerator concepts such as dielectric wall accelerators (DWA) as developed at Lawrence Livermore National Laboratory or laser-plasma accelerators accelerating particles with photons or linac-boosters (LIBOs) combined with other fixed or variable energy accelerators or fixed field alternating gradient synchrotrons (FFAGs). Some embodiments allow the use of the pencil beam scanning technique and a good dose conformation at a limited irradiation/treatment time and a low neutron dose for the patient. The reduced treatment times allow, inter alia, to mitigate drawbacks resulting from organ motion, for example organ motion due to breathing of the patient.

The invention claimed is:

1. A method for treating a non-continuous particle beam produced by an accelerator in order to irradiate a target volume, comprising:
    forming an irradiation spot located in the target volume from the beam, and
    controlling a location of the irradiation spot by setting location controlling elements, wherein at least a portion of the setting of one or more of the location controlling elements takes place in between particle bunches of the beam.

2. The method according to claim 1, wherein the location of the irradiation spot is controlled in three dimensions (X-, Y-, Z-direction) by said location controlling elements and wherein the setting of the location controlling elements in three dimensions (X-, Y-, Z-direction) takes place in between subsequent particle bunches.

3. The method according to claim 1, wherein the non-continuous particle beam is produced by an accelerator, whereby a RF-frequency is changed in a cycle.

4. The method according to claim 3, wherein the accelerator includes a synchrocyclotron comprising a radio frequency (RF) system for alternating an accelerating voltage, and wherein the setting of the location controlling elements is synchronized with the cycle of the RF-frequency.

5. The method according to claim 3, wherein the accelerator includes a synchrocyclotron comprising a radio frequency (RF) system for alternating an accelerating voltage, and wherein the cycle of the RF-frequency is actively interrupted by a control system to allow sufficient time between the particle bunches to finish the setting of the location controlling elements.

6. The method according to claim 3, wherein the accelerator includes a synchrocyclotron comprising a radio frequency (RF) system for alternating an accelerating voltage, and wherein signals from a current diagnostic means measuring beam current and/or signals from the RF-system of the accelerator are used to detect a period between the particle bunches.

7. The method according to claim 3, wherein the accelerator includes a synchrocyclotron comprising a radio frequency (RF) system for alternating an accelerating voltage, and wherein time between subsequent bunches is changed by a control system controlling the RF-system of the accelerator and/or an ion source and/or an input deflector.

8. The method according to claim 1, wherein a number of charged particles in at least one bunch is actively controlled.

9. The method according to claim 8, wherein parameters of the accelerator and/or a beam transport system and/or other elements affecting the beam are set such that the number of charged particles in a single bunch approximately matches a total dose needed for a specific voxel.

10. The method according to claim 8, wherein parameters of the accelerator and/or a beam transport system and/or other elements affecting the beam are set such that the number of charged particles in a single bunch is part of a total dose needed for a specific voxel.

11. The method according to claim 10, wherein each voxel treatment comprises a bunch of a first number of charged particles and is ended with a bunch of a second number of charged particles, wherein the first number is larger than the second number.

12. The method according to claim 10, wherein a dose delivered by each bunch is measured by dose diagnostic means and a control system calculates a desired number of charged particles in a next bunch on the basis of a dose of a preceding bunch and controls elements affecting the beam accordingly.

13. The method according to claim 1, wherein at least one voxel to be irradiated is irradiated with multiple bunches with varying numbers of charged particles.

14. The method according to claim 13, wherein at least one bunch of multiple bunches irradiated to a specific voxel has a number of charged particles whose percentage of a total dose applied to the voxel is not greater than a desired dose precision.

15. The method of claim 1, further comprising actively-controlling a dose of one or more particle bunches delivered to the irradiation spot located in the target volume.

16. A particle beam irradiation apparatus, comprising:
a charged particle accelerator for producing a non-continuous particle beam;
a beam transport system for transporting the particle beam;
a plurality of location controlling elements for varying a location of an irradiation spot in a target volume; and
a control system controlling the location controlling elements in such way that at least a portion of a setting of one or more of the location controlling elements takes place in between particle bunches of the non-continuous particle beam.

17. The apparatus according to claim 16 further comprising charge variation means for varying a number of charged particles per bunch of said particle beam.

18. The apparatus according to claim 17, wherein the charge variation means is a deflector located inside a vacuum chamber of the accelerator.

19. The apparatus according to claim 18, wherein the deflector is adapted to deflect the beam in a direction normal to an accelerating plane such that part of the beam can be stopped by collimator plates mounted above and/or below the accelerating plane.

20. The apparatus according to claim 18, further comprising an ion source adapted to adjust the number of charged particles per bunch.

21. The apparatus according to claim 18, further comprising a RF-system of the accelerator adapted to adjust the number of charged particles per bunch.

22. The apparatus according to claim 18, wherein the deflector is located in a region of the accelerator where the particles being accelerated still have a limited energy.

23. The particle beam irradiation apparatus of claim 16, further comprising a dose diagnostic means for measuring a number of particles per bunch of the non-continuous particle beam, and wherein the control system is further configured to calculate a desired number of particles in a next particle bunch to be delivered to the location of the irradiation spot in the target volume and control the particle beam irradiation apparatus such that the next particle bunch contains the desired number of particles.

24. A method for treating a non-continuous particle beam produced by an accelerator in order to irradiate a target volume, the method comprising:
forming an irradiation spot located in the target volume from the beam, the beam comprising a plurality of particle bunches; and
actively-controlling a number of charged particles in at least one of the plurality of particle bunches.

25. The method of claim 24, wherein actively-controlling further includes:
changing the number of charged particles of the at least one of the plurality of particle bunches in between subsequent particle bunches of the beam.

26. A method for treating a non-continuous particle beam produced by an accelerator in order to irradiate a target volume, the method comprising:
forming an irradiation spot located in the target volume from the beam, the beam comprising a plurality of charged particle bunches;
beginning at least one voxel treatment with a bunch of a first number of charged particles; and
ending the at least one voxel treatment with a bunch of a second number of charged particles, wherein the first number is larger than the second number.

27. A method for treating a non-continuous particle beam produced by an accelerator in order to irradiate a target volume, the method comprising:
forming an irradiation spot located in the target volume from the beam, the beam comprising a plurality of charged particle bunches; and
irradiating at least one of a plurality of voxels to be irradiated with multiple bunches that have varying numbers of charged particles.

* * * * *